(12) United States Patent
Mo et al.

(10) Patent No.: US 6,251,077 B1
(45) Date of Patent: Jun. 26, 2001

(54) METHOD AND APPARATUS FOR DYNAMIC NOISE REDUCTION FOR DOPPLER AUDIO OUTPUT

(75) Inventors: Larry Y. L. Mo, Waukesha; Richard M. Kulakowski, Richfield, both of WI (US)

(73) Assignee: General Electric Company, Milwaukee, WI (US)

(*) Notice: Subject to any disclaimer, the term of this patent is extended or adjusted under 35 U.S.C. 154(b) by 0 days.

(21) Appl. No.: 09/374,713

(22) Filed: Aug. 13, 1999

(51) Int. Cl.[7] ....................................... A61B 8/06
(52) U.S. Cl. ............................................... 600/455
(58) Field of Search ................... 600/440–441, 600/443, 453–456; 73/861.25

(56) References Cited

U.S. PATENT DOCUMENTS

| | | | |
|---|---|---|---|
| 5,647,366 | * 7/1997 | Weng | 600/455 |
| 5,676,148 | * 10/1997 | Koo et al. | 600/447 |
| 5,868,676 | * 2/1999 | McCabe et al. | 600/454 |
| 5,935,074 | * 8/1999 | Mo et al. | 600/454 |

* cited by examiner

Primary Examiner—Francis J. Jaworski
(74) Attorney, Agent, or Firm—Christian G. Cabou; Phyllis Y. Price; Dennis M. Flaherty (57) ABSTRACT

A method and an apparatus for suppressing background noise in spectral Doppler imaging using adaptive noise-reduction low-pass filters. A pair of adaptive low-pass filters are arranged in the two audio Doppler channels for suppressing background noise in the audio Doppler data. The low-pass filtering can be implemented in the frequency domain, i.e., before the IFFT operation, or in the time domain, i.e., after the IFFT operation. Maximum frequency traces are fed into a filter selection block which prescribes the filter cutoffs of the low-pass filters.

25 Claims, 5 Drawing Sheets

METHOD AND APPARATUS FOR DYNAMIC NOISE REDUCTION FOR DOPPLER AUDIO OUTPUT

FIELD OF THE INVENTION

This invention relates to ultrasonic diagnostic systems which measure the velocity of blood flow using spectral Doppler techniques. In particular, the invention relates to the continuous display of such information, including maximum and mean blood flow velocities.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. For blood flow measurements, returning ultrasonic waves are compared to a frequency reference to determine the frequency shifts imparted to the returning waves by moving objects including the vessel walls and the red blood cells inside the vessel. These frequency shifts translate into velocities of motion. An intensity-modulated Doppler frequency versus time spectogram is displayed since the Doppler sample volume or range cell generally contains a distribution of velocities that can vary with time.

In state-of-the-art ultrasonic scanners, the pulsed or continuous wave Doppler waveform is computed and displayed in real-time as a gray-scale spectrogram of velocity versus time with the gray-scale intensity (or color) modulated by the spectral power. The data for each spectral line comprises a multiplicity of frequency data bins for different frequency intervals, the spectral power data in each bin for a respective spectral line being displayed in a respective pixel of a respective column of pixels on the display monitor. Each spectral line represents an instantaneous measurement of blood flow.

In the conventional spectral Doppler mode, an ultrasound transducer array is activated to transmit by a transmit ultrasound burst which is fired repeatedly at a pulse repetition frequency (PRF). The PRF is typically in the kilohertz range. The return radiofrequency (RF) signals are detected by the transducer elements and then formed into a receive beam by a beamformer. For a digital system, the summed RF signal from each firing is demodulated by a demodulator into its in-phase and quadrature (I/Q) components. The I/Q components are integrated (summed) over a specific time interval and then sampled. The summing interval and transmit burst length together define the length of the sample volume as specified by the user. This so-called "sum and dump" operation effectively yields the Doppler signal backscattered from the sample volume. The Doppler signal is passed through a wall filter, which is a high pass filter that rejects any clutter in the signal corresponding to stationary or very slow-moving tissue, including a portion of the vessel wall(s) that might be lying within the sample volume. The filtered output is then fed into a spectrum analyzer, which typically takes Fast Fourier Transforms (FFTS) over a moving time window of 64 to 256 samples. The FFT output contains all the information needed to create the video spectral display as well as the audio output (typical diagnostic Doppler ultrasound frequencies are in the audible range).

For video display, the power spectrum is computed by taking the power or absolute value squared, of the FFT output. The power spectrum is compressed and then displayed via a gray-scale mapping on the monitor as a single spectral line at a particular time point in the Doppler velocity (frequency) versus time spectrogram. The positive frequency [0:PRF/2] spectrum represents flow velocities towards the transducer, whereas the negative frequency [−PRF/2:0] spectrum represents flow away from the transducer. An automatic Doppler maximum/mean waveform tracing is usually performed after the FFT power spectrum has been compressed. The computed maximum/mean velocity traces are usually presented as overlay information on the spectrogram display. More importantly, the values of the maximum frequency ($f_{max}$) trace or "envelope" of the Doppler spectrogram at different points in the cardiac cycle is used in a number of diagnostic indices. In fact, it has been reported that an abnormally high $f_{max}$ or $v_{max}$ at peak systole alone is a good indicator of vascular stenosis. Also, $v_{max}$ is used to estimate the pressure drop across a stenosis based on the Bernoulli equation.

Whereas the mean frequency or velocity is defined by the first moment of the Doppler spectrum, the maximum frequency can be challenging to detect in a consistent manner, especially under weak SNR conditions. In particular, the maximum frequency waveform tracing can be based on the positive frequency spectrum only, the negative frequency spectrum only, or the composite spectrum for which the highest absolute frequency value at each time point is traced.

In an article entitled "Objective algorithm for maximum frequency estimation in Doppler spectral analysers", Med. Biol. Engng. and Comput., Vol. 23, pp. 63–68 (1985), D'Alessio proposed a method of estimating a maximum frequency waveform based on a threshold-crossing technique that takes into account the exponential statistics of the FFT power spectrum of white noise prior to any compression or nonlinear mapping. A modified threshold method and other new methods have also been proposed (see, e.g., Mo et al., "Comparison of four digital maximum frequency estimators for Doppler ultrasound," Ultrasound in Med. & Biol., Vol. 14, pp. 355–363, 1988 and Vaitkus et al., "Development of methods to analyse transcranial Doppler ultrasound signals recorded in microgravity", Med. Biol. Engng. and Comput., Vol. 28, pp. 306–311, 1990), but they are still based on the power spectrum before compression. For realization on a real-time clinical scanner, it is important to trace the mean/maximum frequencies of the compressed spectrum as expressed in gray scale units exactly as they are displayed on the monitor. Unfortunately, the compression (e.g., logarithmic) can substantially alter the statistical distribution of the noise spectral power such that the aforementioned methods are no longer applicable.

An automated method based on the video spectral data is disclosed in U.S. Pat. No. 5,287,753 to Routh et al. The method consists of finding the highest frequency with an intensity equal to a threshold value T, defined as a constant k times an average signal intensity divided by an average noise intensity. The threshold T is updated once every cardiac cycle in order to follow the signal level changes due to changes in instrument setting or movement of the transducer.

An analytic method of tracing the maximum Doppler frequency waveform is taught in U.S. patent application Ser. No. 08/944,119 entitled "Method and Apparatus for Automatic Tracing of Doppler Time-Velocity Waveform Envelope." At the core of this algorithm is a maximum frequency detection mechanism which is based on searching for the highest frequency bin whose spectral amplitude exceeds a certain noise threshold. Unlike the existing methods which require use of one or more empirical constants in setting the threshold level, the method is based on a theoretical noise amplitude distribution in the video spectral domain. In particular, the method of the invention uses a precise model of the statistical distribution of the video spectral power of white noise to establish a threshold for maximum frequency detection. Input to the noise model is the average white noise level in the video spectral display, which can be computed using either of two analytical methods. The predicted threshold versus mean noise level is a highly nonlinear curve, which is key to achieving a robust performance over different display dynamic range settings and SNR conditions For the audio Doppler output, the positive and negative frequency portions, or sidebands, of the FFT output are split into two separate channels representing the forward and reverse flow spectra respectively. For each channel, the sideband is reflected about the zero frequency axis to obtain a symmetric spectrum, which generates, after an inverse FFT (IFFT) operation, a real-valued flow signal in the time domain. Both the forward and reverse flow signals are converted into analog waveforms, which are fed to the corresponding audio speakers.

In a conventional spectral Doppler system, if the Doppler signal is weak, the Doppler signal gain needs to be increased via manual gain control and/or some built-in automatic gain control, in order to visualize and hear the flow signals clearly. Unfortunately, increasing the Doppler gains also tends to boost the background system noise. Since the system noise usually has a flat power spectral density over the frequency range −PRF/2 to +PRF/2 (excluding the wall filter rejection band), boosting its amplitude can generate a distracting "popping" sound in the audio output.

To reduce the background system noise (i.e., popping sound), simple low-pass filters can be applied to the audio Doppler data before or after digital-to-analog conversion. However, such low-pass filters may also remove important high-frequency flow components which, if present, can extend all the way up to ±PRF/2. This problem is complicated by the fact that the frequency bandwidth of the typical blood flow waveforms can vary drastically over the cardiac cycle.

SUMMARY OF THE INVENTION

The invention is a method and an apparatus for suppressing background noise in spectral Doppler imaging using adaptive noise-reduction low-pass filters. In accordance with preferred embodiments, a pair of adaptive low-pass filters are arranged in the two audio Doppler channels for suppressing background noise in the audio Doppler data. The low-pass filtering can be implemented in the frequency domain, i.e., before the IFFT operation, or in the time domain, i.e., after the IFFT operation. In accordance with another preferred embodiment, in some Doppler systems the flow-separated audio Doppler signals may not be obtained by taking the IFFT of the spectral data. Instead, a separate signal processing path may be used to convert the wall filter output directly into forward and reverse flow signals. For such systems, the automatic waveform tracing on the "above" and "below" spectral data would still be performed (as is normally done for diagnostic waveform calculations already), and the resultant spectral traces can be fed into a filter selection block which prescribes the filter cutoffs of time-domain LPFs on the audio Doppler data before the digital-to-analog converters. In accordance with yet another preferred embodiment, the low-pass filters are incorporated in the display processor for suppressing background noise in the video spectral data.

In accordance with each of the foregoing preferred embodiments, each low-pass filter is adaptive in that its frequency cutoff is adjusted dynamically as a function of the flow signal spectrum characteristics. In particular, automatic spectral waveform tracing, which already exists on many conventional spectral Doppler imagers, is utilized to derive the filter cutoffs of the low-pass filters.

DETAILED DESCRIPTION OF THE PREFERRED EMBODIMENTS

Figure 1:
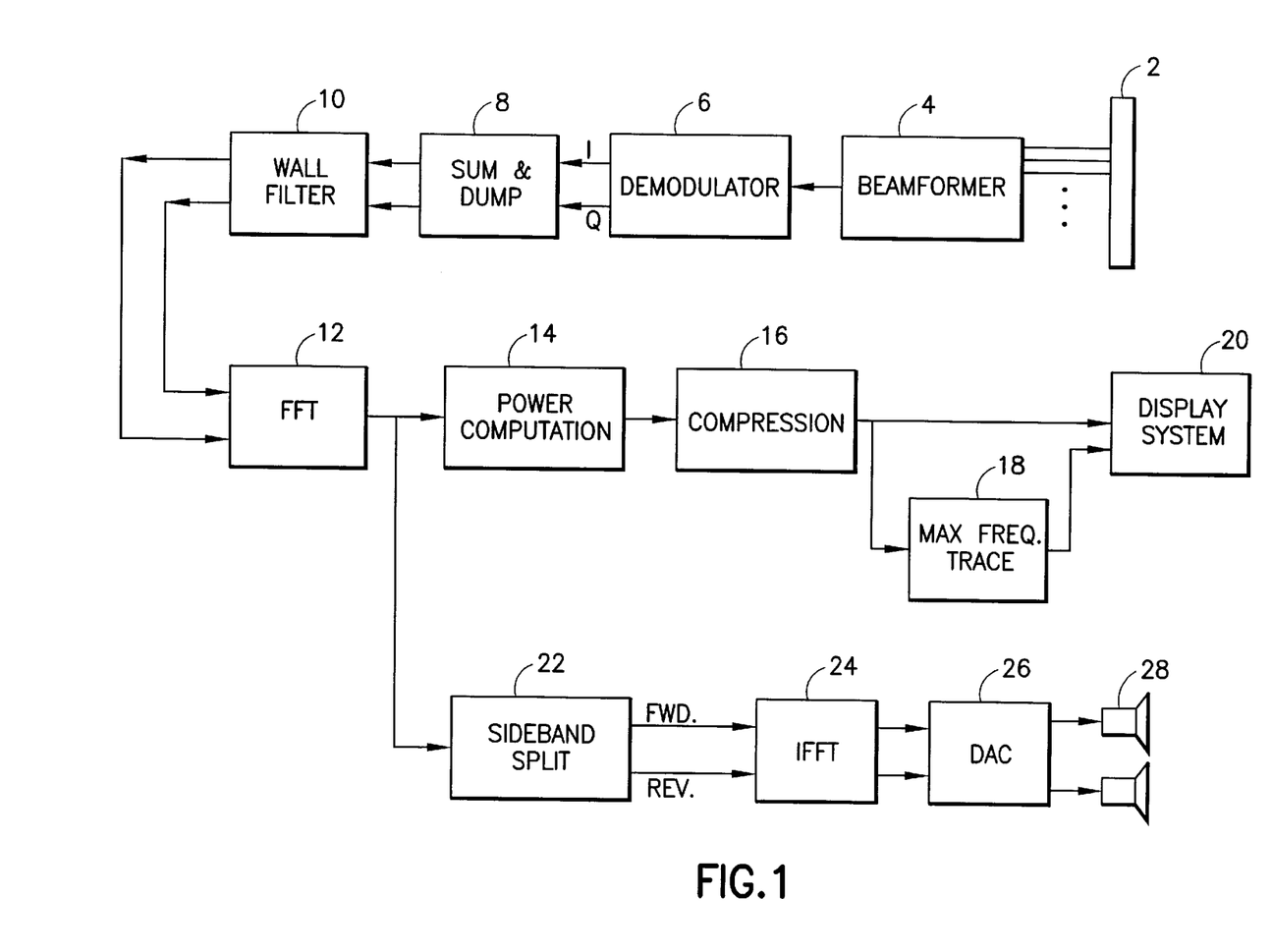
FIG. 1 is a block diagram of the basic signal processing chain in a conventional spectral Doppler imaging system having audio Doppler output.

A typical digital real-time ultrasonic imaging system having a spectral Doppler imaging mode is generally depicted in FIG. 1. An ultrasound transducer array 2 is activated to transmit by a transmit ultrasound burst which is fired repeatedly at a pulse repetition frequency (PRF). The PRF is typically in the kilohertz range. The return RF signals are detected by the transducer elements and then formed into a receive beam by a beamformer 4. For a digital system, the summed RF signal from each firing is demodulated by demodulator 6 into its in-phase and quadrature (I/Q) components. The I/Q components are integrated (summed) over a specific time interval and then sampled by a "sum and dump" block 8. The summing interval and transmit burst length together define the length of the sample volume as specified by the user. The "sum and dump" operation effectively yields the Doppler signal back-scattered from the sample volume. The Doppler signal is passed through a wall filter 10 which rejects any clutter in the signal corresponding to stationary or very slow-moving tissue. The filtered output is then fed into a spectrum analyzer comprising a Fast Fourier Transform (FFT) block 12 and a power computation block 14. The FFT block 14 perform Fast Fourier transformation over a moving time window of 64 to 256 samples. Each FFT power spectrum output by block 14 is compressed (block 16) and sent to a known display system 20 comprising a timeline display memory, a video processor and a display monitor. The video processor maps the compressed FFT power spectral data to a gray scale for display on the monitor as a single spectral line at a particular time point in the Doppler velocity (frequency) versus time spectrogram.

The positive frequency [0:PRF/2] spectrum represents flow velocities towards the transducer, whereas the negative frequency [−PRF/2:0] spectrum represents flow away from the transducer. An automatic Doppler maximum/mean waveform tracing (block 18) is usually performed after the FFT power spectrum has been compressed (block 16). The computed maximum/mean velocity traces are usually presented as overlay information on the spectrogram display.

For the audio Doppler output, the positive and negative frequency portions, or sidebands, of the output of the FFT block 12 are split by a sideband splitter 22 into two separate channels representing the forward and reverse (designated "FWD." and "REV." in FIG. 1) flow spectra respectively. For each channel, the sideband is reflected about the zero frequency axis to obtain a symmetric spectrum, which generates, after an inverse FFT (IFFT) operation (block 24), a real-valued flow signal in the time domain. Both the forward and reverse flow signals are converted into analog waveforms by respective digital-to-analog converters (DACs) 26. The analog waveforms are fed to corresponding audio speakers 28.

Figure 2:
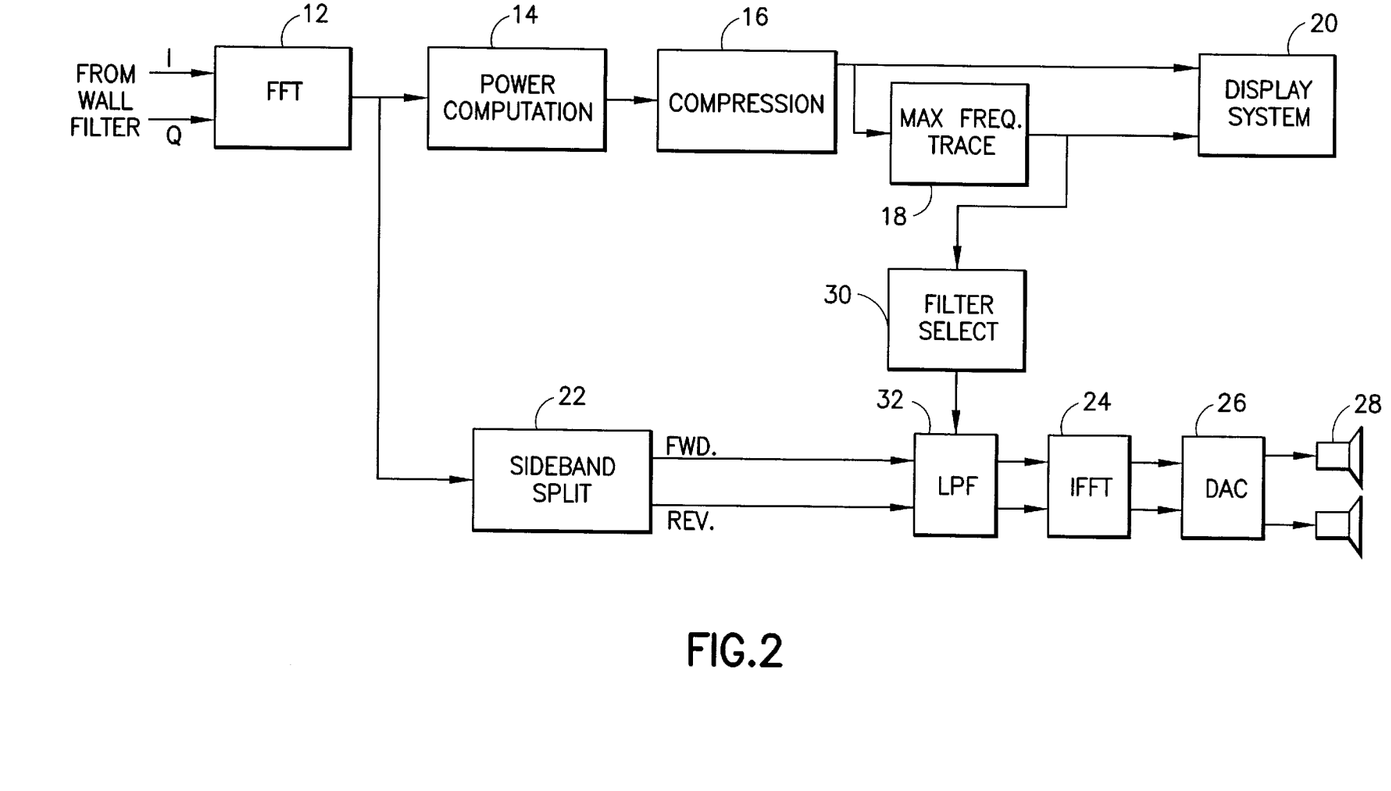
FIG. 2 is a block diagram showing a portion of a spectral Doppler imaging system in accordance with a preferred embodiment of the invention in which the audio Doppler output is low-pass filtered in the frequency domain.

In accordance with one preferred embodiment of the invention, generally depicted in FIG. 2, an adaptive noise reduction low-pass filter (LPF) 32 is inserted in each of the two audio Doppler channels. In this particular embodiment, the low-pass filters 32 are inserted between the sideband splitter 22 and the IFFT block 24. Each low-pass filter 32 is adaptive in that its frequency cutoff is adjusted dynamically as a function of the flow signal spectrum characteristics. In the preferred embodiment shown in FIG. 2, the adaptive low-pass filtering can be implemented as follows:

1) The automatic maximum frequency waveform tracing (block 18) is run separately on the spectral data above and below the baseline (i.e., on both the positive and negative frequency spectra).

2) The "above" and "below" spectral traces are fed separately to a filter selection block 30. The filter selection block 30 may utilize a trace conditioner to first remove any extraneous noise spike or trace drop-out. Such a trace conditioner can be implemented using a variety of standard smoothing techniques, including a moving-average over the past several trace values, or a median filter.

3) The respective conditioned trace values (i.e., maximum frequencies) are then used to set the cutoff frequencies of the noise-reduction low-pass filters. For example, the cutoff frequency $f_{max}$ may be set at, e.g., 20% above the trace values. The cutoff frequencies of the noise-reduction low-pass filters 32 for the "above" and "below" spectral data are set independently based on the "above" and "below" trace data respectively.

4) The noise-reduction low-pass filters 32 for the "above" and "below" spectral data are effected in the frequency domain by multiplying the low-pass filter frequency responses with the forward/reverse FFT spectral data. As illustrated in the one-sided frequency plot of FIG. 3, each low-pass filter should be designed with a smooth transition band to avoid filter transients after IFFT.

Figure 3:
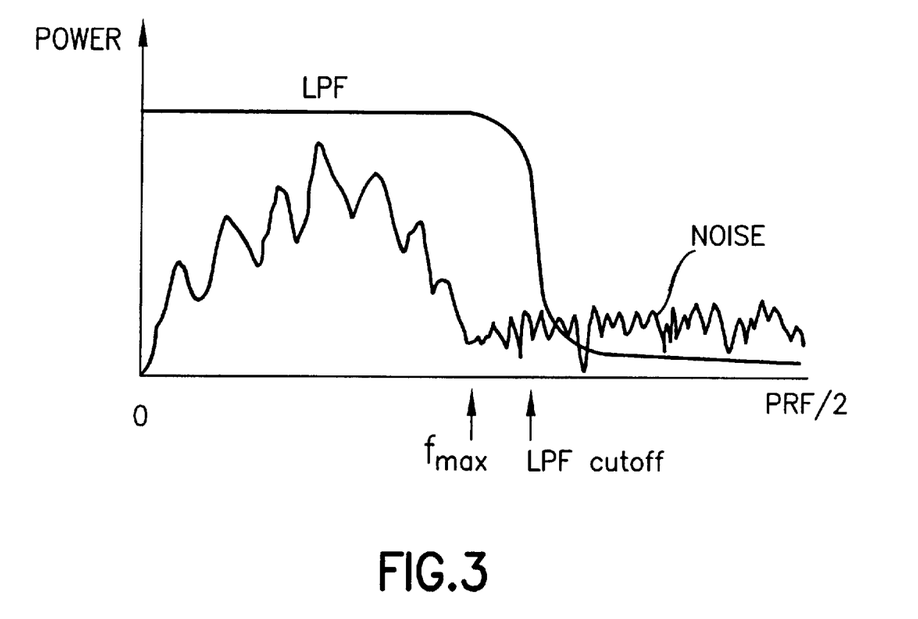
FIG. 3 is a graph of signal power versus frequency wherein the bold line indicates the response of a low-pass filter having a flat passband in accordance with one preferred embodiment of the invention. $f_{max}$ is the maximum frequency trace value.
Figure 4:
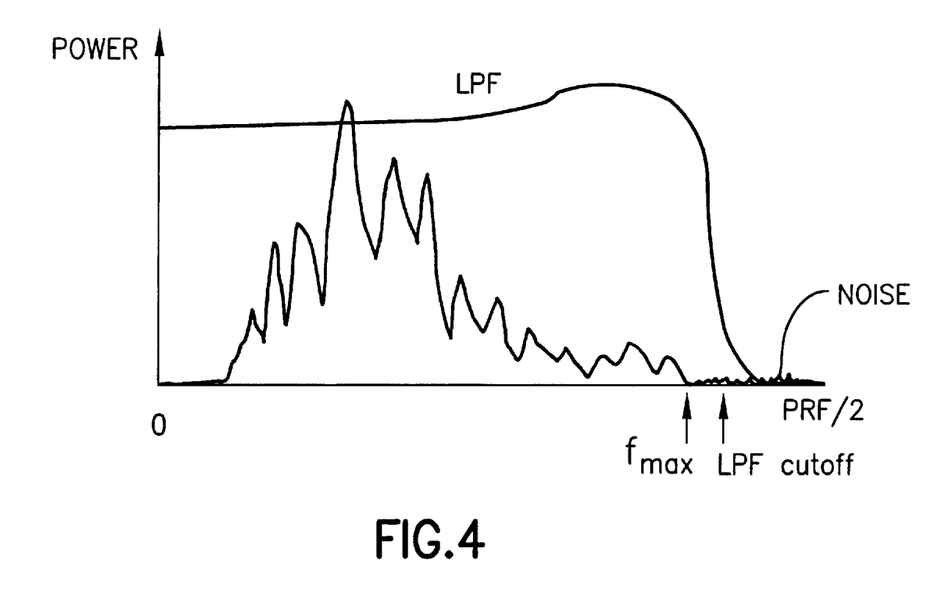
FIG. 4 is a graph of signal power versus frequency wherein the bold line indicates the response of a low-pass filter having a high cutoff and a passband which is slightly elevated as it approaches the transition band in accordance with another preferred embodiment of the invention.

5) For the purpose of noise reduction only, the filter passband can be flat, as shown in FIG. 3. Optionally, for filters with a high cutoff (close to ±PRF/2), the filter passband may be slightly elevated as it approaches the transition band, as shown in FIG. 4, to enhance the high-frequency components of the flow spectrum. That is, the low-pass filter can serve as an equalization filter and/or a noise-reduction filter.

6) The IFFT operations (block 24) are performed on the low-pass-filtered spectral data to obtain the flow-separated audio signals as in a conventional Doppler system, but with reduced background noise.

Figure 7:
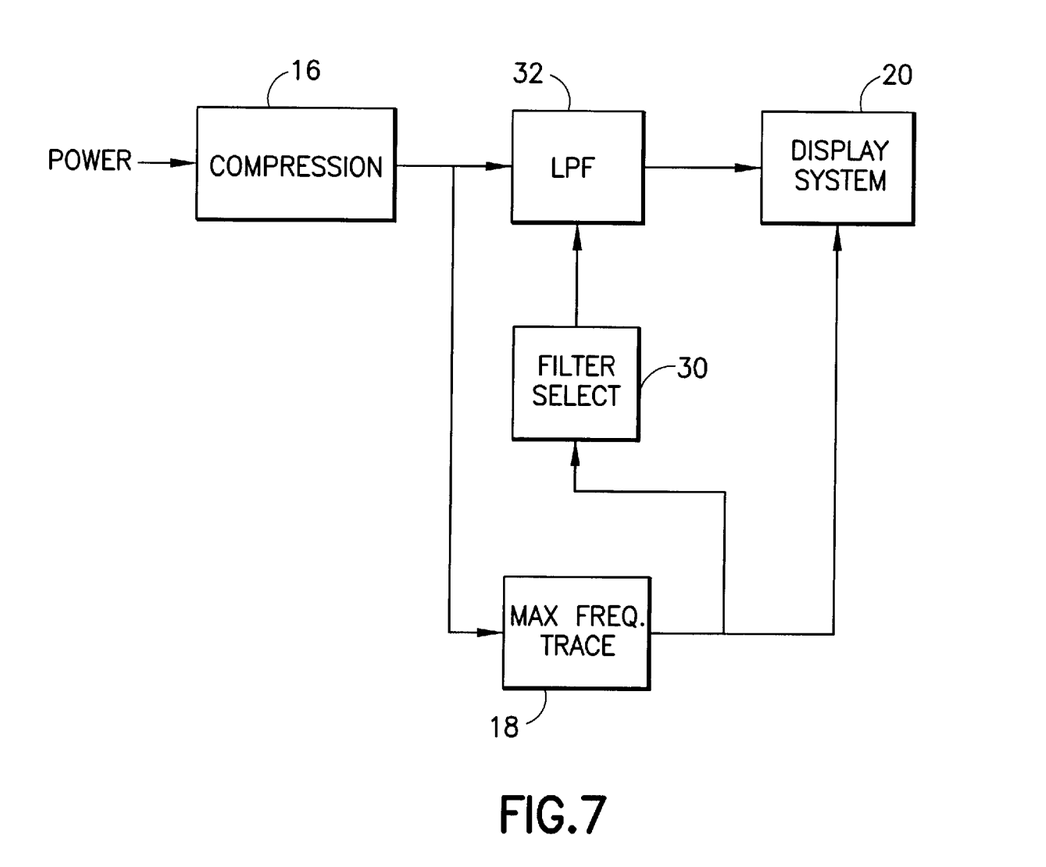
FIG. 7 is a block diagram showing low-pass filtering of the video spectral output in the frequency domain in accordance with another preferred embodiment of the invention.

In accordance with an alternative preferred embodiment, shown in FIG. 7, the video spectral noise can be reduced. Similar noise-suppression low-pass filters 32 (which filter in the frequency domain) can be applied to the compressed video spectral data output from the compression block 16. The filter select block 30 in FIG. 7 operates in the same manner described above for filter select block 30 in FIG. 2.

Figure 5:
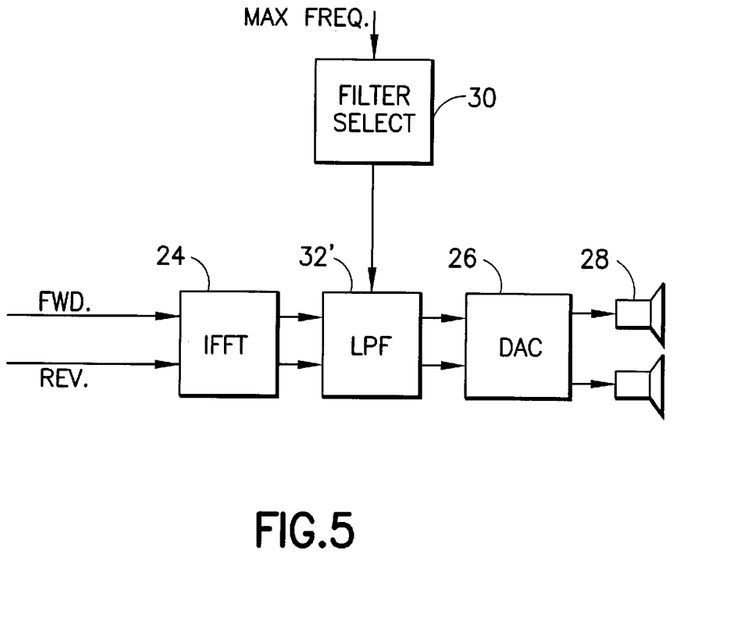
FIGS. 5 and 6 are block diagrams showing low-pass filtering of the audio Doppler output in the time domain in accordance with other alternative preferred embodiments of the invention.

In accordance with the foregoing preferred embodiments, automatic spectral waveform tracing (which already exists on many premium scanners) is used to drive the filter cutoffs of low-pass filters in order to suppress background noise in the audio Doppler or video spectral data. It should be obvious to those skilled in the art that the specific implementations can vary for different system configurations. For example, the noise-suppression low-pass filter 32' (see FIG. 5) can be implemented in the time domain after the IFFT operation (block 24), even though the frequency domain implementation as described above is simpler.

Figure 6:
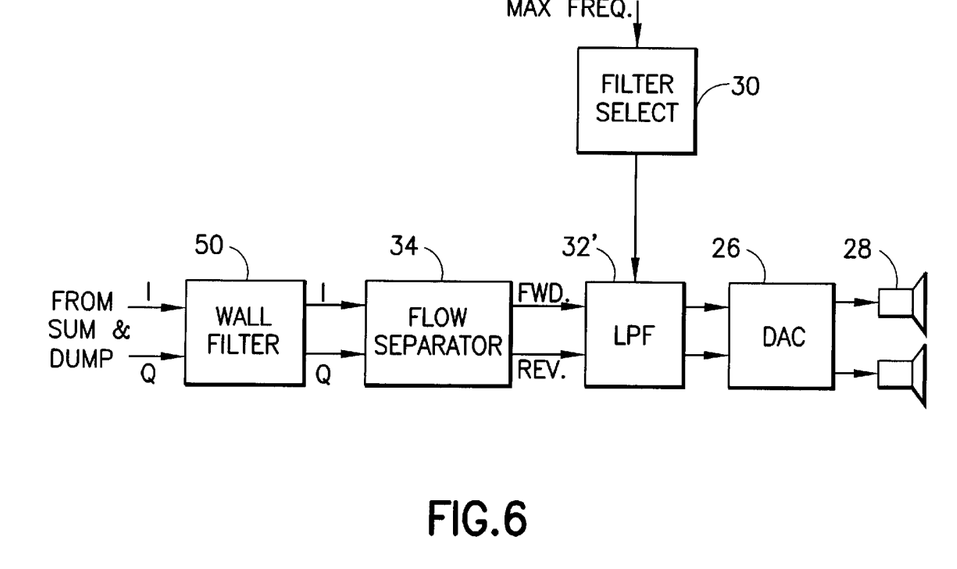

As another example, in some Doppler systems the flow-separated audio Doppler signals are not obtained by taking the IFFT of the spectral data. Instead, a separate signal processing path, e.g., flow separator 34, may be used to convert the output of wall filter 10 directly into forward and reverse flow signals. For such systems, the automatic waveform tracing on the "above" and "below" spectral data would still be performed (as is normally done for diagnostic waveform calculations already), and the resultant spectral (e.g., maximum frequency) traces can be fed into a filter selection block 30 which prescribes the filter cutoffs of time-domain low-pass filters 32' before the audio Doppler data is sent to the digital-to-analog converters 26.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. In particular, it should be clear to those skilled in the art that the techniques as shown in FIGS. 2 and 5–7 can be implemented in hardware (e.g., a digital signal processor) and/or computer software (e.g., software of a host computer incorporated in an ultrasound imaging system. Therefore, it is intended that the invention not be limited to the particular embodiment disclosed as the best mode contemplated for carrying out this invention, but that the invention will include all embodiments falling within the scope of the appended claims. As used in the claims the term "digital signal processor" includes digital signal processing hardware and/or software.

What is claimed is:

1. A system for producing audible sound waves from electrical signals representing sequences of samples of Doppler signals acquired from a sample volume containing moving ultrasound scatterers, comprising:

a digital signal processor for processing Doppler signal samples to produce maximum frequency data representing the maximum velocities over time of ultrasound scatterers in said sample volume and directional flow data representing the flow of ultrasound scatterers in a predetermined direction in said sample volume;

a low-pass filter arranged to suppress noise in said directional flow data;

a cutoff frequency selector for adaptively setting the cutoff frequency of said low-pass filter as a function of said maximum frequency data; and an audio subsystem for generating audible sound waves which are a function of the output of said low-pass filter.

2. The system as recited in claim 1, wherein said low-pass filter filters in the frequency domain.

3. The system as recited in claim 1, wherein said low-pass filter filters in the time domain.

4. The system as recited in claim 1, further comprising:

a transmitter for transmitting a multiplicity of pulses of ultrasound into a sample volume of ultrasound scatterers in succession;

a receiver for acquiring a respective sequence of successive samples of Doppler signals following each pulse; and a demodulator for demodulating said Doppler signal samples into in-phase and quadrature components, wherein said digital signal processor comprises:

first and second wall filters for substantially rejecting clutter in the in-phase and quadrature components corresponding to stationary or very slow-moving tissue;

a spectrum analyzer for producing spectral data by Fast Fourier transformation of the wall-filtered in-phase and quadrature components;

means for extracting frequency-domain directional flow data from said spectral data; and means for transforming said frequency-domain directional flow data into time-domain directional flow data.

5. The system as recited in claim 4, wherein said low-pass filter is arranged between said means for extracting frequency-domain directional flow data from said spectral data and said means for transforming said frequency-domain directional flow data into time-domain directional flow data.

6. The system as recited in claim 4, wherein said low-pass filter is arranged between said means for transforming said frequency-domain directional flow data into time-domain directional flow data and said audio subsystem.

7. The system as recited in claim 1, further comprising:

a transmitter for transmitting a multiplicity of pulses of ultrasound into a sample volume of ultrasound scatterers in succession;

a receiver for acquiring a respective sequence of successive samples of Doppler signals following each pulse; and a demodulator for demodulating said Doppler signal samples into in-phase and quadrature components, wherein said digital signal processor comprises:

first and second wall filters for substantially rejecting clutter in the in-phase and quadrature components corresponding to stationary or very slow-moving tissue; and means for extracting said directional flow data from said in-phase and quadrature components, and said low-pass filter is arranged between said means for extracting said directional flow data from said in-phase and quadrature components and said audio subsystem.

8. A system for displaying spectral data from electrical signals representing sequences of samples of Doppler signals acquired from a sample volume containing moving ultrasound scatterers, comprising:

a digital signal processor for processing Doppler signal samples to produce spectral data representing the velocities over time of ultrasound scatterers in said sample volume, and processing said spectral data to produce maximum frequency trace data representing the maximum velocities over time;

a low-pass filter arranged to suppress noise in said spectral data;

a cutoff frequency selector for adaptively setting the cutoff frequency of said low-pass filter as a function of said maximum frequency trace data; and function of said maximum frequency trace data; and a display system for displaying said low-pass-filtered spectral data and said maximum frequency trace data.

9. A method for producing audible sound waves from electrical signals representing sequences of samples of Doppler signals acquired from a sample volume containing moving ultrasound scatterers, comprising the steps of:

processing Doppler signal samples to produce maximum frequency data representing the maximum velocities over time of ultrasound scatterers in said sample volume;

processing said Doppler signal samples to produce directional flow data representing the flow of ultrasound scatterers in a predetermined direction in said sample volume;

adaptively setting the cutoff frequency of a low-pass filter as a function of said maximum frequency trace data;

low-pass filtering said directional flow data using said low-pass filter to suppress noise; and generating audible sound waves which are a function of the output of said low-pass filter.

10. The method as recited in claim 9, wherein said low-pass filtering is performed in the frequency domain.

11. The method as recited in claim 9, wherein said low-pass filtering is performed in the time domain.

12. The method as recited in claim 9, wherein said step of adaptively setting the cutoff frequency of the low-pass filter comprises the step of setting said cutoff frequency to be greater than the respective values of said maximum frequency trace data by a predetermined percentage.

13. The method as recited in claim 9, further comprising the step of smoothing said maximum frequency trace data prior to adaptively setting the cutoff frequency.

14. A system for producing audible sound waves from electrical signals representing sequences of samples of Doppler signals acquired from a sample volume containing moving ultrasound scatterers, comprising:

means for processing Doppler signal samples to produce maximum frequency data representing the maximum velocities over time of ultrasound scatterers in said sample volume;

means for processing said Doppler signal samples to produce directional flow data representing the flow of ultrasound scatterers in a predetermined direction in said sample volume;

a low-pass filter for suppressing noise in said directional flow data;

means for adaptively setting the cutoff frequency of said low-pass filter as a function of said maximum frequency trace data; and means for generating audible sound waves which are a function of the output of said low-pass filter.

15. A method for displaying spectral data from electrical signals representing sequences of samples of Doppler signals acquired from a sample volume containing moving ultrasound scatterers, comprising the steps of:

processing Doppler signal samples to produce spectral data representing the velocities over time of ultrasound scatterers in said sample volume;

processing said spectral data to produce maximum frequency trace data representing the maximum velocities over time;

adaptively setting the cutoff frequency of a low-pass filter as a function of said maximum frequency trace data;

low-pass filtering said spectral data using said low-pass filter to suppress noise; and displaying said low-pass-filtered spectral data and said maximum frequency trace data.

16. The method as recited in claim 15, wherein said step of adaptively setting the cutoff frequency of the low-pass filter comprises the step of setting said cutoff frequency to be greater than the respective values of said maximum frequency trace data by a predetermined percentage.

17. The method as recited in claim 15, further comprising the step of smoothing said maximum frequency trace data prior to adaptively setting the cutoff frequency.

18. A system for displaying spectral data from electrical signals representing sequences of samples of Doppler signals acquired from a sample volume containing moving ultrasound scatterers, comprising:

means for processing Doppler signal samples to produce spectral data representing the velocities over time of ultrasound scatterers in said sample volume;

means for processing said spectral data to produce maximum frequency trace data representing the maximum velocities over time;

a low-pass filter arranged to suppress noise in said spectral data;

a cutoff frequency selector for adaptively setting the cutoff frequency of said low-pass filter as a function of said maximum frequency trace data; and a display system for displaying said low-pass-filtered spectral data and said maximum frequency trace data.

19. The system as recited in claim 18, wherein said means for adaptively setting the cutoff frequency of the low-pass filter comprises means for setting said cutoff frequency to be greater than the respective values of said maximum frequency trace data by a predetermined percentage.

20. The system as recited in claim 18, further comprising means for smoothing said maximum frequency trace data prior to adaptively setting the cutoff frequency.

21. A method for producing audible sounds representing flow of ultrasound scatterers, comprising the steps of:

transmitting pulses of ultrasound into a sample volume containing moving ultrasound scatterers;

acquiring a multiplicity of successive samples of Doppler signals backscattered from said sample volume;

rejecting clutter in said Doppler signals corresponding to stationary or very slow-moving tissue;

analyzing the frequency spectrum of said Doppler signals to form spectral data;

deriving maximum frequency trace data from said spectral data for flow in a predetermined direction;

adaptively setting the cutoff frequency of a low-pass filter as a function of said maximum frequency trace data;

extracting frequency-domain directional flow data corresponding to flow in said predetermined direction from said spectral data;

low-pass filtering said frequency-domain directional flow data in the low-pass filter;

transforming said low-pass-filtered frequency-domain directional flow data into time-domain directional flow data;

converting said time-domain directional flow data into analog audio signals; and feeding said analog audio signals into an audio speaker.

22. The method as recited in claim 21, wherein said step of adaptively setting the cutoff frequency of the low-pass filter comprises the step of setting said cutoff frequency to be greater than the respective values of said maximum frequency trace data by a predetermined percentage.

23. The method as recited in claim 21, further comprising the step of smoothing said maximum frequency trace data prior to adaptively setting the cutoff frequency.

24. A method for producing audible sounds representing flow of ultrasound scatterers, comprising the steps of:

transmitting pulses of ultrasound into a sample volume containing moving ultrasound scatterers;

acquiring a multiplicity of successive samples of Doppler signals backscattered from said sample volume;

rejecting clutter in said Doppler signals corresponding to stationary or very slow-moving tissue;

analyzing the frequency spectrum of said Doppler signals to form spectral data;

deriving maximum frequency trace data from said spectral data for flow in a predetermined direction;

adaptively setting the cutoff frequency of a low-pass filter as a function of said maximum frequency trace data;

extracting frequency-domain directional flow data corresponding to flow in said predetermined direction from said spectral data;

transforming said frequency-domain directional flow data into time-domain directional flow data;

low-pass filtering said time-domain directional flow data in the low-pass filter;

converting said low-pass-filtered time-domain directional flow data into analog audio signals; and feeding said analog audio Doppler signals into an audio speaker.

25. A method for producing audible sounds representing flow of ultrasound scatterers, comprising the steps of:

transmitting pulses of ultrasound into a sample volume containing moving ultrasound scatterers;

acquiring a multiplicity of successive samples of Doppler signals backscattered from said sample volume;

wall filtering said Doppler signals to reject clutter corresponding to stationary or very slow-moving tissue;

analyzing the frequency spectrum of said wall-filtered Doppler signals to form spectral data;

deriving maximum frequency trace data from said spectral data for flow in a predetermined direction;

adaptively setting the cutoff frequency of a low-pass filter as a function of said maximum frequency trace data;

extracting directional flow data corresponding to flow in said predetermined direction from said wall-filtered Doppler signals;

low-pass filtering said directional flow data in the low-pass filter;

converting said low-pass-filtered directional flow data into analog audio signals; and feeding said analog audio Doppler signals into an audio speaker.

* * * * *

UNITED STATES PATENT AND TRADEMARK OFFICE
CERTIFICATE OF CORRECTION

PATENT NO. : 6,251,077 B1
DATED : June 26, 2001
INVENTOR(S) : Larry Y.L. Mo, Richard M. Kulakowski It is certified that error appears in the above-identified patent and that said Letters Patent is hereby corrected as shown below:

Column 8, claim 8,
Line 9, after the word "and" delete "function of said maximum frequency trace data; and"

Signed and Sealed this

Eighth Day of January, 2002

Attest:

Attesting Officer

JAMES E. ROGAN
Director of the United States Patent and Trademark Office